United States Patent [19]
Fuller, Jr et al.

[11] Patent Number: 5,210,330
[45] Date of Patent: May 11, 1993

[54] PROCESS FOR THE PREPARATION OF PHENYLHYDROQUINONE

[75] Inventors: Dewey W. Fuller, Jr, Bristol; Bruce L. Gustafson, Kingsport; Bobby L. Bernard, Rogersville, all of Tenn.

[73] Assignee: Eastman Kodak Company, Rochester, N.Y.

[21] Appl. No.: 748,592

[22] Filed: Aug. 22, 1991

[51] Int. Cl.$^5$ .................... C07C 39/12; C07C 37/06
[52] U.S. Cl. .................................................. 568/747
[58] Field of Search ................. 568/731, 743, 744, 747

[56] References Cited

U.S. PATENT DOCUMENTS

| 4,798,911 | 1/1989 | Lentz et al. | 568/747 |
| 4,847,429 | 7/1989 | Fuller et al. | 268/643 |

FOREIGN PATENT DOCUMENTS

| 0346913 | 12/1989 | European Pat. Off. | 568/743 |
| 535279 | 1/1977 | U.S.S.R. | 568/772 |
| 89/00987 | 2/1989 | World Int. Prop. O. | 568/747 |

Primary Examiner—Warren B. Lone
Attorney, Agent, or Firm—J. Frederick Thomsen; William P. Heath, Jr.

[57] ABSTRACT

Disclosed is an improved process for the preparation of phenylhydroquinone wherein hydroquinone is first alkylated with cyclohexene to produce cyclohexylhydroquinone which is then dehydrogenated to obtain phenylhydroquinone. The improvement comprises carrying out both the alkylation and dehydrogenation reactions in the presence of a solvent comprising diphenyl ether, biphenyl or a mixture thereof. The solvent possesses selective solubility for hydroquinone and cyclohexylhydroquinone which permits the separation of unreacted hydroquinone from the alkylation reaction product. The boiling point of the solvent also permits the dehydrogenation reaction to be performed at substantially atmospheric pressure.

6 Claims, No Drawings

PROCESS FOR THE PREPARATION OF PHENYLHYDROQUINONE

This invention pertains to the manufacture of phenylhydroquinone from cyclohexene and hydroquinone. More specifically, this invention pertains to a process wherein cyclohexene and hydroquinone are reacted in the presence of certain heterogenous, acidic catalysts and high boiling solvents and the cyclohexylhydroquinone thus obtained is catalytically dehydrogenated without isolation to produce phenylhydroquinone. The process also includes an intermediate step wherein unreacted hydroquinone is selectively recovered from the high-boiling solvent.

U.S. Pat. No. 4,847,429 discloses a process for the preparation of phenylhydroquinone by the steps of (1) reacting hydroquinone and cyclohexene, or a cyclohexene precursor such as cyclohexanol, in the presence of an acidic catalyst such as 85% aqueous phosphoric acid to obtain cyclohexylhydroquinone and (2) catalytically dehydrogenating the cyclohexylhydroquinone to produce phenylhydroquinone. The procedure specifically disclosed in this patent involves the steps of (1) reacting cyclohexene and hydroquinone in the presence of 85% aqueous phosphoric acid, (2) twice extracting the reaction mixture of (1) with toluene, (3) distilling the toluene extracts of (2) at 0.6 torr to separate the toluene and the cyclohexylhydroquinone, and (4) catalytically dehydrogenating the cyclohexylhydroquinone to produce phenylhydroquinone. While the process disclosed in U.S. Pat. No. 4,847,429 provides a useful process for the manufacture of phenylhydroquinone, it can be practiced in commercial-scale equipment only with great difficulty.

In the preparation of cyclohexylhydroquinone by the alkylation of hydroquinone with cyclohexene, dialkylation of the hydroquinone to form di-(cyclohexyl)hydroquinone can constitute a significant loss in yield based on hydroquinone. This problem may be minimized by performing the alkylation in a manner which results in a relatively low degree of conversion of the hydroquinone. For example, when the conversion of hydroquinone is maintained at about 40 mole percent during the alkylation of hydroquinone with cyclohexene, the mole ratio of mono-cyclohexylhydroquinone to di-(cyclohexyl)hydroquinone typically is approximately 40:1. However, when the alkylation is carried out at a hydroquinone conversion of 80 mole percent, the mole ratio of mono-substituted to di-substituted product decreases dramatically to approximately 7:1. It is apparent that the use of procedures which provide lower hydroquinone conversions presents a problem relative to the recovery of unreacted hydroquinone from the crude reaction product containing the cyclohexylhydroquinone. The recovery of hydroquinone by conventional distillation procedures is not practical due to the tendency of hydroquinone to sublime, which causes fouling of the distillation equipment and, eventually, the plugging of process lines.

We have found that phenylhydroquinone may be manufactured from hydroquinone and cyclohexene, or a precursor of cyclohexene such as cyclohexanol, in good to excellent chemical yields based on the hydroquinone used by carrying out the alkylation and dehydrogenation reactions in the presence of an inert, organic solvent comprising diphenyl ether, biphenyl, methyl naphthalene or a mixture thereof. The use of such materials as the process solvent provides a plurality of advantages. The primary advantage resides in the selective solubilities of hydroquinone and cyclohexylhydroquinone in diphenyl ether, biphenyl and/or methyl naphthalene. At alkylation temperatures, the solubility of hydroquinone in diphenyl ether, biphenyl and/or methyl naphthalene is sufficient to permit good to excellent reaction rates of hydroquinone and cyclohexene. Upon cooling the crude product effluent from the alkylation reactor, the cyclohexylhydroquinone remains in solution whereas most of the unconverted hydroquinone comes out of solution (precipitates) and can be recovered by conventional solid/liquid separation techniques such as centrifugation or filtration.

A second advantage afforded by the diphenyl ether, biphenyl and/or methyl naphthalene solvent is that it may be used as the process solvent in both the alkylation procedure and the subsequent dehydrogenation of cyclohexylhydroquinone to phenylhydroquinone. Thus, isolation of the cyclohexylhydroquinone is not required prior to the dehydrogenation step. Furthermore, the boiling point (256°–288° C.) of diphenyl ether, biphenyl and methyl naphthalene permits the dehydrogenation step to be performed at atmospheric pressure using general purpose equipment. The material referred to herein as methyl naphthalene is a catalytic reformer petroleum distillate (CAS 68477-31-6) supplied as Methyl Naphthalene No. 5.

Our invention therefore provides a process for the manufacture of phenylhydroquinone comprising the steps of:

(1) alkylating hydroquinone with cyclohexene in an alkylation zone at an alkylating effective temperature in the presence of a heterogenous, acidic, alkylation catalyst and a solvent comprising diphenyl ether, biphenyl, methyl naphthalene or a mixture thereof to achieve a hydroquinone conversion of less than about 80 mole percent to produce a crude alkylation product mixture comprising catalyst, hydroquinone, cyclohexylhydroquinone and solvent;

(2) reducing the temperature of the crude alkylation product mixture by at least 50° C. to precipitate hydroquinone therefrom;

(3) separating hydroquinone from the mixture of step (2) to obtain a solution comprising cyclohexylhydroquinone and solvent;

(4) feeding the solution obtained in step (3) to a dehydrogenation zone wherein the cyclohexylhydroquinone is dehydrogenated in the presence of a dehydrogenation catalyst to obtain a solution of phenylhydroquinone in the solvent.

The process may include an additional step wherein the solution obtained from step (3) is concentrated by vaporizing some of the solvent prior to feeding the solution to the dehydrogenation zone. The phenylhydroquinone produced in step (4) may be isolated by distillation. Alternatively, acetic anhydride may be added to the solution obtained from step (4) to convert the phenylhydroquinone to phenylhydroquinone diacetate.

The first step of the process is carried out by contacting a solution of hydroquinone and cyclohexene in a solvent comprising diphenyl ether, biphenyl, methyl naphthalene or a mixture thereof with a heterogeneous, acidic, alkylation catalyst at alkylation-effective temperature typically used in hydroquinone alkylation reactions. Typically, the alkylation temperature is at least 100° C., e.g., from 100° to 250° C., with alkylation temperatures of about 155° to 200° C. being preferred. Although super-atmospheric pressure may be used, e.g., pressures of about 1 to 35 bars (absolute), the alkylation pressure normally is carried out at a pressure of less than about 7 bars and preferably at approximately ambient pressure.

The heterogeneous, acidic, alkylation catalyst may be selected from various acidic materials which are insoluble or essentially insoluble in the process solvent. Examples of such materials include acidic ion exchange resins, acidic molecular sieves and silica-alumina materials. The catalyst preferably is selected from the acidic faujasite zeolites such as the hydrogen form of Y zeolite. The catalyst may be employed in the alkylation zone in the form of a slurry of catalyst powder or beads or as a fixed bed of catalyst pellets. When a slurry of the catalyst is used, the amount of catalyst employed normally is at least 0.01 weight percent, preferably about 0.7 to 5.0 weight percent, of the total weight of the reaction mixture within the alkylation zone.

The solvent used in our novel process preferably is selected from diphenyl ether and mixtures of diphenyl ether and biphenyl wherein diphenyl ether constitutes at least 50 weight percent of the mixture. The heat transfer materials supplied under the Dowtherm tradename are examples of suitable solvents. Dowtherm A consists essentially of 25 weight percent biphenyl and 75 weight percent diphenyl ether.

The relative amounts of hydroquinone and cyclohexene fed to the alkylation zone may vary significantly depending, for example, on such variables as the alkylation temperature being used, the residence time within the alkylation zone and the particular alkylation catalyst. In accordance with our invention, the formation of undesired di-(cyclohexyl)hydroquinone is suppressed by maintaining the mole percent hydroquinone converted to cyclohexylhydroquinone at an average value of less than about 80. The mole percent hydroquinone conversion may be achieved by the selection of a particular hydroquinone:cyclohexene feed ratio for use in combination with a particular catalyst, reaction temperature and residence time.

Hydroquinone and cyclohexene may be charged or fed to the alkylation zone in a cyclohexene:hydroquinone mole ratio of about 0.1:1 to about 2:1. It is preferred that substantially all, e.g., at least 90 mole percent, of the cyclohexene be consumed during the alkylation reaction and therefore the reactants preferably are fed or charged in a cyclohexene:hydroquinone mole ratio of about 0.4:1 to 0.8:1. The reaction time or, in the case of continuous operation, the residence time within the alkylation zone is dependent on the variables described above. However, the reaction or residence time usually is in the range of 1 to 8 hours.

The crude product effluent from the alkylation zone typically contains about 3 to 6 weight percent hydroquinone, about 10 to 20 weight percent cyclohexylhydroquinone, up to about 4 weight percent di-(cyclohexyl)hydroquinone and up to 0.8 weight percent of other by-products such as p-cyclohexyloxyphenol and cyclohexyldiphenyl ether isomers with the remainder being primarily solvent. When using a catalyst slurry, the crude product also may comprise a minor amount of catalyst. The crude product effluent is cooled to a temperature at least 50° C. less than the temperature within the alkylation zone to precipitate a substantial amount, e.g., at least 60 weight percent, of the hydroquinone present. The temperature of the alkylation product preferably is reduced to about 30° to 100° C., and most preferably to about 50° to 80° C., to precipitate at least about 70 weight percent of the hydroquinone. The hydroquinone (and any catalyst) present in the crude product mixture after the temperature reduction is recovered by conventional solid/liquid separation techniques such as centrifugation or filtration and may be recycled to the alkylation zone.

The solution remaining after the recovery of the hydroquinone is fed to a dehydrogenation zone wherein the cyclohexylhydroquinone component of the solution is converted to phenylhydroquinone. To minimize the size of the equipment constituting the dehydrogenation zone, the volume of the cyclohexylhydroquinone-containing solution is reduced by 30 to 50 volume percent. The volume reduction is accomplished simply by heating the solution to vaporize the desired amount of process solvent which may be recovered and used to prepare a hydroquinone solution for the alkylation zone. Typically, the cyclohexylhydroquinone concentration of the solution after the volume reduction is in the range of about 20 to 50 weight percent. We have found that the presence of significant amounts of hydroquinone in the cyclohexylhydroquinone-containing solution can be detrimental to the dehydrogenation step of the process. Therefore, it is preferred that the cyclohexylhydroquinone-containing solution used in the dehydrogenation zone contain less than about 1 weight percent hydroquinone.

The conversion of cyclohexylhydroquinone to phenylhydroquinone in the dehydrogenation zone may be carried out according to known procedures, e.g., the procedures described in U.S. Pat. No. 4,847,429, the disclosure of which is incorporated herein by reference. Generally, the dehydrogenation is carried out in the presence of a catalytic amount of a heterogenous, dehydrogenation catalyst at a temperature of at least 200° C. and preferably under boiling conditions, i.e., at the boiling point of the process solvent. The dehydrogenation preferably is carried out at approximately ambient pressure although pressures of about 0.01 to 1 bar (absolute) may be used.

The preferred catalysts comprise the Group VIII noble metals deposited on a suitable support material such as carbon, especially supported, Group VIII noble metal catalysts which have been treated with a modifying agent such as copper or sulfur to produce a modified catalyst which does not cause decomposition of the hydroquinone moiety, e.g., by hydrogenolysis of the phenolic hydroxyl groups. Examples of such modified catalysts include sulfided palladium on alumina, sulfided palladium on carbon, sulfided platinum on carbon, sulfided platinum on alumina and palladium-copper on carbon.

The dehydrogenation may be carried out in the liquid phase with agitation while passing an inert gas such as nitrogen through the reaction mixture to facilitate the removal of the hydrogen produced. The flow rate of inert gas typically is within the range of 1 to 10,000 L per hour of inert gas per L of the cyclohexylhydroquinone-containing solution contained within the dehydrogenation zone.

The phenylhydroquinone may be recovered in a purity of 99% or greater using conventional isolation and refining procedures. For example, after filtering the product mixture from the dehydrogenation zone to remove catalyst, the phenylhydroquinone-containing solution may be distilled under reduced pressure to remove solvent and by products and then the phenylhydroquinone product (boiling point=224° C. at 14 torr). Alternatively, the phenylhydroquinone may be converted to its diacetate ester by the addition of acetic anhydride to the filtered, phenylhydroquinone-containing solution. The phenylhydroquinone diacetate then may be isolated by distillation as described above.

The process of the present invention is further illustrated by the following example. The alkylation reaction was carried out in a 22-liter, 3-necked flask equipped with a thermometer, mechanical stirrer, a condenser and a bottom drain valve. The alkylation product mixture was drained through a filter into a second 22-liter, 3-necked flask (solution concentration flask) equipped with the filter, a stirrer, a distillation head connected to a receiver and a vacuum source, wherein a portion of the process solvent was removed from the cyclohexylhydroquinone product solution.

The dehydrogenation reaction was carried out in a 12-liter, 4-necked flask equipped with a nitrogen feed tube, a stirrer, a septum port for sampling, a condenser vented to a dry ice trap, a bottom drain valve and a heating mantle. The dehydrogenation reaction product was drained from the dehydrogenation flask through a filter into a flask from which the phenylhydroquinone was isolated by distillation under reduced pressure or in which the phenylhydroquinone was converted to phenylhydroquinone diacetate by reaction with acetic acid. In the latter case, the solution containing the phenylhydroquinone diacetate was transferred to yet another 12-liter flask for recovery of the diester product by distillation.

The analytical values reported were determined by capillary gas chromatography and the identity of all materials was confirmed by gas chromatography/mass spectrometry.

Diphenyl ether (14,850 g), hydroquinone (2960 g, 26.91 mol), LZY-74 zeolite alkylation catalyst (250 g) and cyclohexene (1104 g, 13.46 mol) were charged to the alkylation flask and heated to 155° C. The mixture was stirred at 155±2° C. for a period of 5 hours and then allowed to cool to 55° C. The reaction mixture was sampled and analyzed first when the mixture reached 155° C. (time 0) and then each hour thereafter for 4 hours. The results of the analyses are shown below wherein the values given are weight percents, Time is in hours, CH is cyclohexene, HQ is hydroquinone, DPE is diphenyl ether, CHHQ is cyclohexylhydroquinoe and DiCHHQ is dicyclohexylhydroquinone.

| Time | CH | HQ | DPE | CHHQ | DiCHHQ |
|---|---|---|---|---|---|
| 0 | 2.47 | 11.36 | 74.71 | 4.62 | 0.19 |
| 1 | 0.41 | 8.85 | 74.35 | 10.31 | 0.71 |
| 2 | 0.14 | 8.55 | 73.91 | 11.08 | 0.63 |
| 3 | 0.05 | 8.48 | 74.09 | 11.32 | 0.66 |
| 4 | 0.02 | 8.49 | 74.58 | 11.49 | 0.69 |

The mixture also contained minor amounts of by-products such as cyclohexyldiphenyl ether and p-cyclohexyloxyphenol.

The alkylation product mixture was filtered into the solution concentration flask, the filter cake collected was stirred with 6 liters of diphenyl ether for 2 hours at 60° C. and the filter cake slurry was filtered into the concentration flask. The alkylation product solution was concentrated by heating at 132°–143° C. at a pressure of 10 torr to distill off approximately 14 liters of diphenyl ether over a period of about 8 hours. The concentrated product solution weighed 4924 g and contained 0.76 weight percent hydroquinone, 27.07 weight percent cyclohexylhydroquinone and 2.33 weight percent dicyclohexylhydroquinone. The final filter cake (filter solids) weighed 6237 g and contained 24.23 weight percent hydroquinone, 53.14 weight percent diphenyl ether, 15.30 weight percent cyclohexylhydroquinone and 0.39 weight percent dicyclohexylhydroquinone.

The concentrated alkylation product solution and 132 g of water-wet (52% water), sulfided 5% palladium on carbon catalyst (Mallinkrodt Inc. E-180) were charged to the dehydrogenation flask and the mixture was heated to reflux temperature (approximately 260° C). The mixture was maintained at reflux for 26 hours while sparging nitrogen to the flask at the rate of 2 standard cubic feet per hour and then was cooled to 160° C. and filtered into the product recovery flask. Samples were taken and analyzed when the reaction mixture first reached 260° C. (Time 0) and every 2 hours thereafter during the 26-hour reaction period. The results of some of those analyses are shown below wherein PHQ refers to phenylhydroquinone and Time and CHHQ have the meanings specified above.

| Time | PHQ | CHHQ |
|---|---|---|
| 0 | 2.52 | 24.37 |
| 4 | 11.68 | 13.65 |
| 8 | 18.37 | 7.07 |
| 12 | 21.45 | 3.83 |
| 16 | 23.55 | 2.10 |
| 20 | 23.15 | 1.03 |
| 24 | 25.01 | 0.64 |
| 26 | 24.71 | 0.50 |

The dehydrogenation product solution was distilled at 15 torr to separate the phenylhydroquinone from the solvent and by products. The fraction removed at a distillation head temperature of about 221°–224° C. weighed 735 g and consisted of 95.64 weight percent phenylhydroquinone.

The invention has been described in detail with particular reference to preferred embodiments thereof, but it will be understood that variations and modifications may be effected within the spirit and scope of the invention.

We claim:

1. Process for the manufacture of phenylhydroquinone comprising the steps of:
   (1) alkylating hydroquinone with cyclohexene in an alkylation zone at an alkylating-effective temperature in the presence of a heterogenous, acidic, alkylation catalyst and a solvent comprising diphenyl ether, biphenyl, methyl naphthalene or a mixture thereof to achieve a hydroquinone conversion of not more than about 80 mole percent to produce a crude alkylation product mixture comprising catalyst, hydroquinone, cyclohexylhydroquinone and solvent;
   (2) reducing the temperature of the crude alkylation product mixture by at least 50° C. to precipitate hydroquinone therefrom;
   (3) separating hydroquinone from the mixture of step (2) to obtain a solution comprising cyclohexylhydroquinone and solvent; and
   (4) feeding the solution obtained in step (3) to a dehydrogenation zone wherein the cyclohexylhydroquinone is dehydrogenated in the presence of a dehydrogenation catalyst to obtain a solution of phenylhydroquinone in the solvent.

2. Process according to claim 1 wherein step (1) is carried out at a temperature of about 155° to 200° C. in the presence of a solvent comprising diphenyl ether or diphenyl ether containing up to about 50 weight percent biphenyl and step (2) comprises reducing the temperature of the alkylation product mixture to about 30° to 100° C.

3. Process for the manufacture of phenylhydroquinone comprising the steps of:
   (1) alkylating hydroquinone with cyclohexene in an alkylation zone wherein the cyclohexene:hydroquinone mole ratio is about 0.4:1 to 0.8:1 at a temperature of about 155° to 200° C. in the presence of a heterogenous, acidic, alkylation catalyst and a solvent comprising diphenyl ether or diphenyl ether containing up to about 50 weight percent biphenyl to achieve a hydroquinone conversion of not more than about 80 mole percent to produce a crude alkylation product mixture comprising catalyst, hydroquinone, cyclohexylhydroquinone and solvent;
   (2) reducing the temperature of the crude alkylation product mixture to about 30° to 100° C. to precipitate hydroquinone therefrom;
   (3) separating hydroquinone from the mixture of step (2) to obtain a solution comprising cyclohexylhydroquinone and solvent; and
   (4) feeding the solution obtained in step (3) to a dehydrogenation zone wherein the cyclohexylhydroquinone is dehydrogenated at a temperature of at least 200° C. in the presence of a dehydrogenation catalyst to obtain a solution of phenylhydroquinone in the solvent.

4. Process according to claim 3 wherein step (2) comprises reducing the temperature of the alkylation product mixture to about 50° to 80° C. and step (4) is carried out at approximately ambient pressure and at the boiling point of the solvent.

5. Process for the manufacture of phenylhydroquinone comprising the steps of:
   (1) alkylating hydroquinone with cyclohexene in an alkylation zone wherein the cyclohexene:hydroquinone mole ratio is about 0.4:1 to 0.8:1 at a temperature of about 155° to 200° C. in the presence of a heterogenous, acidic, alkylation catalyst selected from the acidic faujasite zeolites and a solvent comprising diphenyl ether or diphenyl ether containing up to about 50 weight percent biphenyl to achieve a hydroquinone conversion of not more than about 80 mole percent to produce a crude alkylation product mixture comprising catalyst, hydroquinone, cyclohexylhydroquinone and solvent;
   (2) reducing the temperature of the crude alkylation product mixture to about 50° to 80° C. to precipitate hydroquinone therefrom;
   (3) separating hydroquinone from the mixture of step (2) to obtain a solution comprising cyclohexylhydroquinone and solvent; and
   (4) feeding the solution obtained in step (3) to a dehydrogenation zone wherein the cyclohexylhydroquinone is dehydrogenated at a temperature of at least 200° C. in the presence of a dehydrogenation catalyst to obtain a solution of phenylhydroquinone in the solvent.

6. Process according to claim 5 wherein the solution obtained in step (3) contains less than about 1 weight percent hydroquinone and step (4) is carried out at approximately ambient pressure and at the boiling point of the solvent in the presence of sulfided palladium catalyst.

* * * * *